US012806370B2

(12) United States Patent
Ma

(10) Patent No.: US 12,806,370 B2
(45) **Date of Patent: *Nov. 24, 2026**

(54) BLOOD CONTROL SEPTUM AND RELATED SYSTEMS

(71) Applicant: Becton, Dickinson and Company, Franklin Lakes, NJ (US)

(72) Inventor: Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 310 days.

This patent is subject to a terminal disclaimer.

(21) Appl. No.: 17/718,582

(22) Filed: Apr. 12, 2022

(65) Prior Publication Data

US 2022/0233813 A1 Jul. 28, 2022

Related U.S. Application Data

(63) Continuation of application No. 16/515,962, filed on Jul. 18, 2019, now Pat. No. 11,324,919.

(60) Provisional application No. 62/716,723, filed on Aug. 9, 2018.

(51) Int. Cl.

| | |
|---|---|
| ***A61M 39/06*** | (2006.01) |
| ***A61M 25/00*** | (2006.01) |
| ***A61M 25/06*** | (2006.01) |
| *A61M 25/01* | (2006.01) |

(52) U.S. Cl.

CPC .... *A61M 25/0043* (2013.01); *A61M 25/0023* (2013.01); *A61M 25/0606* (2013.01); *A61M 2025/0188* (2013.01)

(58) Field of Classification Search

CPC .... A61M 2025/0188; A61M 2039/062; A61M 2039/0633; A61M 2039/066; A61M 39/0693

See application file for complete search history.

(56) References Cited

U.S. PATENT DOCUMENTS

| | | | | |
|---|---|---|---|---|
| 9,126,012 | B2 * | 9/2015 | Mckinnon ......... | A61M 25/0097 |
| 11,324,919 | B2 * | 5/2022 | Ma .................... | A61M 25/0023 |
| 2003/0060804 | A1 | 3/2003 | Vaillancourt | |
| 2007/0282268 | A1 | 12/2007 | Mayse | |

(Continued)

FOREIGN PATENT DOCUMENTS

| | | |
|---|---|---|
| EP | 3028737 | 6/2016 |
| JP | 2014528807 A | 10/2014 |
| JP | 2015508010 A | 3/2015 |

(Continued)

*Primary Examiner* — Deanna K Hall

(74) *Attorney, Agent, or Firm* — Kirton McConkie; Whitney Blair; Kevin Stinger

(57) ABSTRACT

A catheter assembly may include a catheter adapter, which may include a distal end, a proximal end, and a lumen extending therethrough. The catheter assembly may also include a septum slidably disposed within the lumen. The septum may include a distal end, a proximal end, and a barrier disposed between the distal end of the septum and the proximal end of the septum. The barrier may divide an interior of the septum into a distal cavity and a proximal cavity. A distal face of the barrier may include a protrusion. The barrier may include a slit extending through the protrusion for selectively opening fluid communication between the distal cavity and the proximal cavity.

20 Claims, 7 Drawing Sheets

(56) References Cited

U.S. PATENT DOCUMENTS

| | | | | |
|---|---|---|---|---|
| 2013/0218082 | A1* | 8/2013 | Hyer ................ | A61M 25/0097 604/256 |
| 2014/0228775 | A1* | 8/2014 | Burkholz .......... | A61M 39/0693 604/244 |

FOREIGN PATENT DOCUMENTS

| | | | |
|---|---|---|---|
| JP | 2016506855 | A | 3/2016 |
| WO | 2010/093791 | A1 | 8/2010 |
| WO | 2010/111285 | | 9/2010 |

* cited by examiner

BLOOD CONTROL SEPTUM AND RELATED SYSTEMS

RELATED APPLICATIONS

This application is a continuation of U.S. application Ser. No. 16/515,962, filed Jul. 18, 2019, and entitled BLOOD CONTROL SEPTUM AND RELATED SYSTEMS, which claims the benefit of U.S. application Ser. No. 62/716,723, filed Aug. 9, 2018, and entitled BLOOD CONTROL SEPTUM AND RELATED SYSTEMS, which are incorporated herein in their entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing up away from skin of the patient. The PIVC and introducer needle are generally inserted at a shallow angle through the skin into vasculature of the patient.

In order to verify proper placement of the introducer needle and/or the PIVC in the vein, a user generally confirms that there is "flashback" of blood in a flashback chamber of a PIVC assembly. Once placement of the needle has been confirmed, the user may temporarily occlude flow in the vein and remove the introducer needle, leaving the PIVC in place within the vein. The user may also attach a device to the PIVC assembly for fluid infusion and/or blood withdrawal. This process has been somewhat difficult in practice since many PIVC placement sites simply do not allow easy occlusion of the vein. Additionally, even when such occlusion is achieved, it may be imperfect, resulting in blood leaking from the PIVC assembly housing the PIVC and endangering medical personnel.

PIVC assemblies have thus been provided in the art that provide a variety of seals or "septa" for preventing outflow of fluid during and following removal of the introducer needle from the vein. However, in some instances, blood may leak through a particular septum after the introducer needle is removed and before the user has time to connect the device to the PIVC assembly for fluid infusion or blood withdrawal. Leakage through the septum may occur more quickly particularly when the introducer needle has a large outer diameter. Accordingly, it would be an advancement in the art to provide a septum that controls the flow of blood and reduces leakage during the steps surrounding placement and use of a PIVC.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to septa for blood control, as well as related devices, systems, and methods. In some embodiments, a catheter assembly may include a catheter adapter, which may include a distal end, a proximal end, and a lumen extending therethrough. In some embodiments, the catheter assembly may also include a septum slidably disposed within the lumen. In some embodiments, the septum may include a distal end, a proximal end, and a barrier disposed between the distal end of the septum and the proximal end of the septum. In some embodiments, the barrier may divide an interior of the septum into a distal cavity and a proximal cavity. In some embodiments, a distal face of the barrier may include a protrusion. In some embodiments, the barrier may include a slit extending through the protrusion for selectively opening fluid communication between the distal cavity and the proximal cavity.

In some embodiments, in response to reflux blood flowing against the protrusion, opposing faces of the slit may press against each other more tightly to seal the slit. This may be due to radial forces of the reflux blood on the protrusion as well as axial forces of the reflux blood on the protrusion. In some embodiments, as the axial forces act on a center portion of the protrusion, pushing the center portion of the protrusion axially in a proximal direction, the opposing faces of the slit move toward each other in greater interference.

In some embodiments, the protrusion may be disposed at a center of the distal face. In some embodiments, the slit may extend through a center of the protrusion. In some embodiments, a proximal face of the barrier may be flat. In some embodiments, the protrusion may be symmetric.

In some embodiments, at least a portion of an outer surface of the protrusion may be disposed at an acute angle with respect to a transverse axis of the catheter assembly. For example, the protrusion may include a dome. In some embodiments, a diameter of the dome may be greater than a diameter of the slit. As another example, the protrusion may include a truncated dome. In some embodiments, a diameter of a truncated portion of the truncated dome may be greater than a diameter of the slit. As yet another example, the protrusion may include a truncated cone. In some embodiments, a diameter of a truncated portion of the truncated cone may be greater than the diameter of the slit.

In some embodiments, a septum actuator may be fixed within the lumen of the catheter adapter. In some embodiments, the septum may be configured to move between a proximal position and a distal position in response to insertion of a separate device into the proximal end of the catheter adapter. In some embodiments, the septum actuator may penetrate the slit in response to movement of the septum from the proximal position to the distal position. In some embodiments, the slit may extend through a center of the protrusion, and the septum actuator may be disposed within the slit and the center of the protrusion when the septum is disposed in the distal position.

In some embodiments, the protrusion may be spaced apart from and adjacent the septum actuator when the septum is in the proximal position prior to insertion of the separate device. In other embodiments, the septum actuator may contact an outer surface of the protrusion but may not penetrate the slit when the septum is in the proximal position prior to insertion of the separate device.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
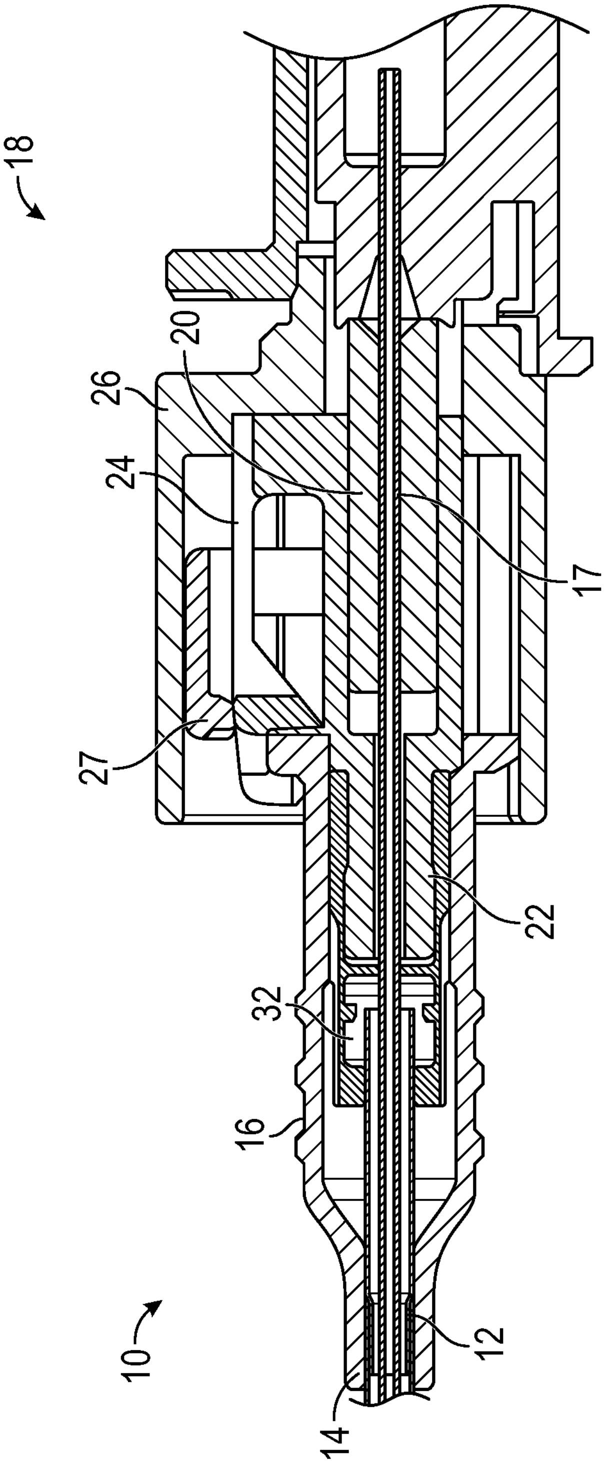
FIG. 1A (Prior Art)
FIG. 1A is a cross-sectional view of an example catheter assembly of the prior art, illustrating the catheter assembly in an insertion or ready for use position, according to some embodiments.
Figure 1B:
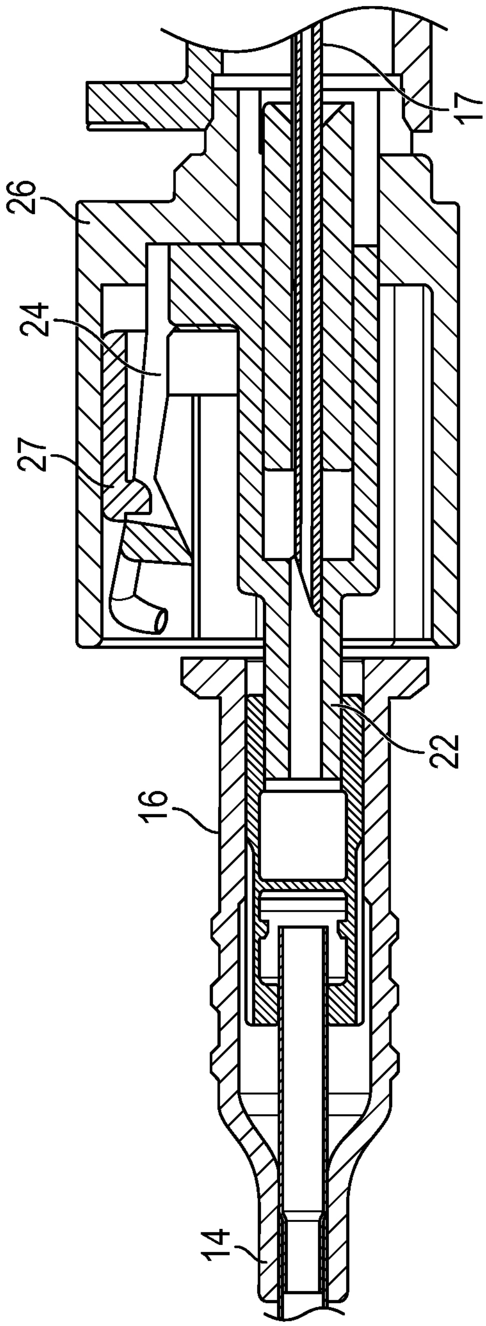
FIG. 1B (Prior Art)
FIG. 1B is another cross-sectional view of the catheter assembly of FIG. 1A, illustrating the catheter assembly in a safe position, according to some embodiments.

The present disclosure relates generally to a septum for blood control, as well as related devices, systems, and methods. Referring now to FIGS. 1A-1B, a catheter assembly 10 of the prior art is illustrated. FIG. 1A illustrates the catheter assembly 10 in a first, ready for use position. The catheter assembly 10 may correspond to Smiths Medical ViaValve® Safety IV Catheter with Blood Control. The catheter assembly 10 generally includes a catheter 12 coupled to a distal end 14 of a catheter adapter 16. In the ready for use position, the catheter 12 is positioned over an introducer needle 17 with the sharp tip of the introducer needle 17 extending from a distal end of the catheter 12.

The catheter assembly 10 generally includes a safety coupling 18, which includes an actuator 20, a nose 22, and an engagement arm 24. A collar 26 of the safety coupling 18 is positioned about a proximal portion of the catheter adapter 16, the engagement arm 24, and the actuator 20. In this respect, the collar 26 can inhibit access to these components or portions thereof. The safety coupling 18 is constructed to engage the catheter adapter 16 with the engagement arm 24 when the catheter assembly 10 is in the ready for use position with the actuator 20 shifted to a distal, engaged position. In the ready for use position, the engagement arm 24 is held in contact with the catheter adapter 16 by an engaging portion 27 of the actuator 20.

Referring now to FIG. 1B, the catheter assembly 10 is illustrated in a second, safe position. When the catheter assembly 10 is in the safe position, the actuator 20 is shifted to a proximal, disengaged position. In the safe position, the engagement arm 24 is released from engagement with the catheter adapter 16, thereby enabling the safety coupling 18 and the introducer needle 17 to be removed from the catheter 12 and the catheter adapter 16.

Figure 1C:
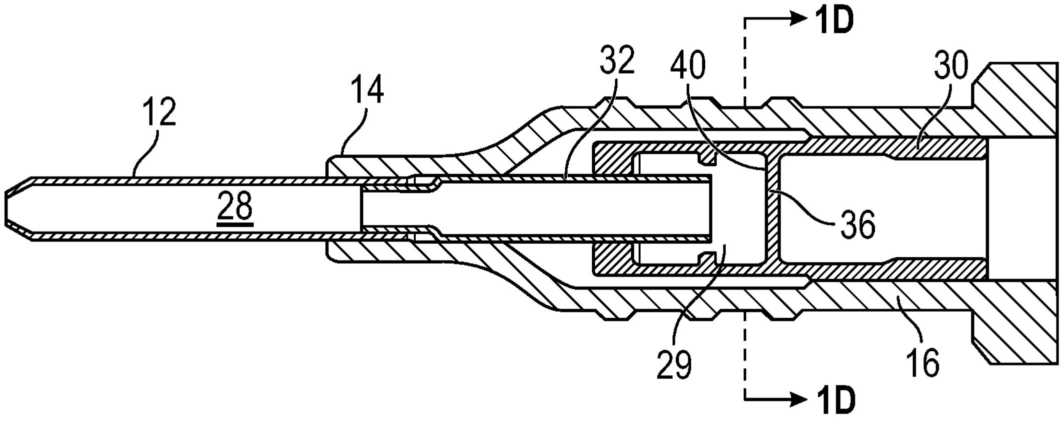
FIG. 1C (Prior Art)
FIG. 1C is another cross-sectional view of the catheter assembly of FIG. 1A with an example safety coupling and example introducer needle removed, according to some embodiments.

Referring now to FIG. 1C, the catheter assembly 10 is illustrated with the safety coupling 18 and the introducer needle 17 removed. A lumen 29 of the catheter adapter 16 is in fluid communication with a lumen 28 of the catheter 12. Once inserted into a patient, the catheter 12 and the catheter adapter 16 provide a fluid conduit to facilitate delivery of a fluid to and/or retrieval of a fluid from a patient.

Figure 1D:
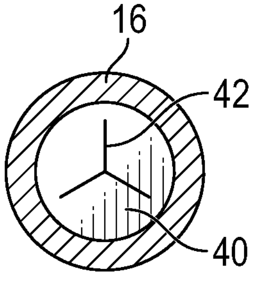
FIG. 1D is a cross-sectional view of the catheter assembly of FIG. 1C along the line 1D-1D of FIG. 1C, according to some embodiments.

The catheter assembly 10 includes a septum 30 slidably housed with the lumen 29 of the catheter adapter 16. The catheter assembly 10 also includes a septum actuator 32, which is generally fixedly positioned within a distal fluid chamber 34. The septum 30 is tube shaped having a barrier 36 disposed between a distal end and a proximal end of the septum 30. The barrier 36 divides an interior of the septum 30 into the distal fluid chamber 34 and a proximal fluid chamber 38. A distal face 40 of the barrier 36 is flat. Referring now to FIG. 1D, a Y-shaped slit 42 is formed in the barrier 36 for selectively opening fluid communication between the distal fluid chamber 34 and the proximal fluid chamber 38. However, in some instances, when the slit 42 is closed, fluid may leak through the slit 42.

Figure 2A:
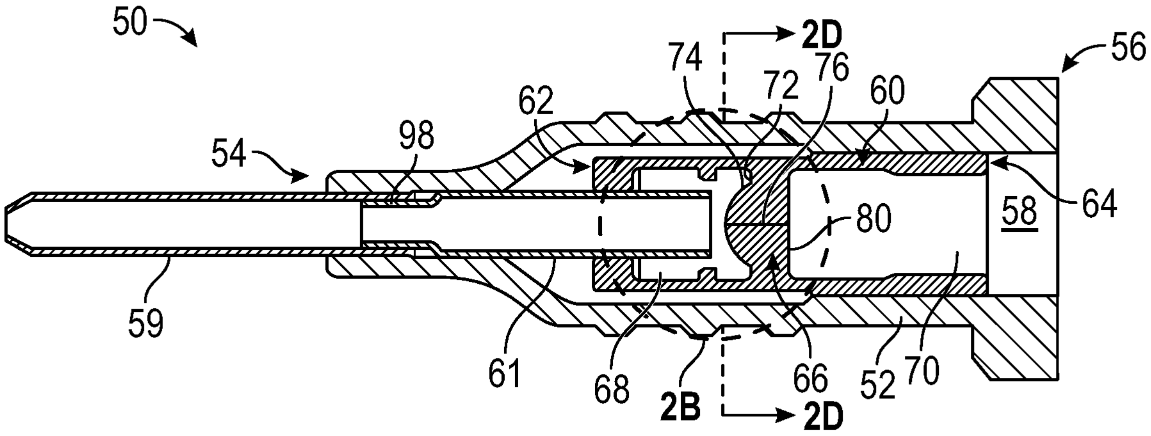
FIG. 2A is a cross-sectional view of another example catheter assembly, illustrating an example septum having an example protrusion, according to some embodiments.

Referring now to FIG. 2A, a catheter assembly 50 is illustrated, according to some embodiments. In some embodiments, the catheter assembly 50 may include or correspond to the catheter system 10. In some embodiments, the catheter assembly 50 may include one or more features or elements of the catheter system 10. In some embodiments, the catheter system 50 may include the safety coupling 18 and/or the introducer needle 17.

In some embodiments, the catheter assembly 50 may include a catheter adapter 52, which may include a distal end 54, a proximal end 56, and a lumen 58 extending therethrough. In some embodiments, a catheter 59 may extend distally from the catheter adapter 52. In some embodiments, the catheter 59 may include a peripheral intravenous catheter ("PIVC").

In some embodiments, the catheter assembly 50 may also include a septum 60 slidably disposed within the lumen 58. In some embodiments, the septum 60 may be constructed of an elastomeric or resilient material. In some embodiments, a septum actuator 61 may be fixed within the lumen 58 of the catheter adapter 52. In some embodiments, the septum 60 may include a distal end 62, a proximal end 64, and a barrier 66 disposed between the distal end 62 of the septum 60 and the proximal end 64 of the septum 60. In some embodiments, the barrier 66 may divide an interior of the septum 60 into a distal cavity 68 and a proximal cavity 70. In some embodiments, the septum 60 may control or limit passage of fluid between the distal cavity 68 and the proximal cavity 70.

In some embodiments, the septum 60 may include a flexible or semi-flexible polymer plug having an outer diameter that is configured to fit within the lumen 58. In some embodiments, the septum 60 may be held in place within the lumen 58 via contact with one or more inner surfaces of the internal lumen, contact with anti-pathogenic material, or another suitable means. In some embodiments, the barrier 66 may be disposed at or near the distal end 62 or proximal end 64 of the septum 60. In some embodiments, the septum 60 may have a substantially H-shaped cross section.

In some embodiments, a distal face 72 of the barrier 66 may include a protrusion 74. In some embodiments, the barrier 66 may include a slit 76 extending through the protrusion 74 for selectively opening fluid communication between the distal cavity 68 and the proximal cavity 70. In some embodiments, the protrusion 74 may be disposed at a center of the distal face 72. In some embodiments, the slit 76 may extend through a center of the protrusion 74. In some embodiments, a proximal face 80 of the barrier 66 may be flat. In some embodiments, the protrusion 74 may be symmetric.

Figure 2B:
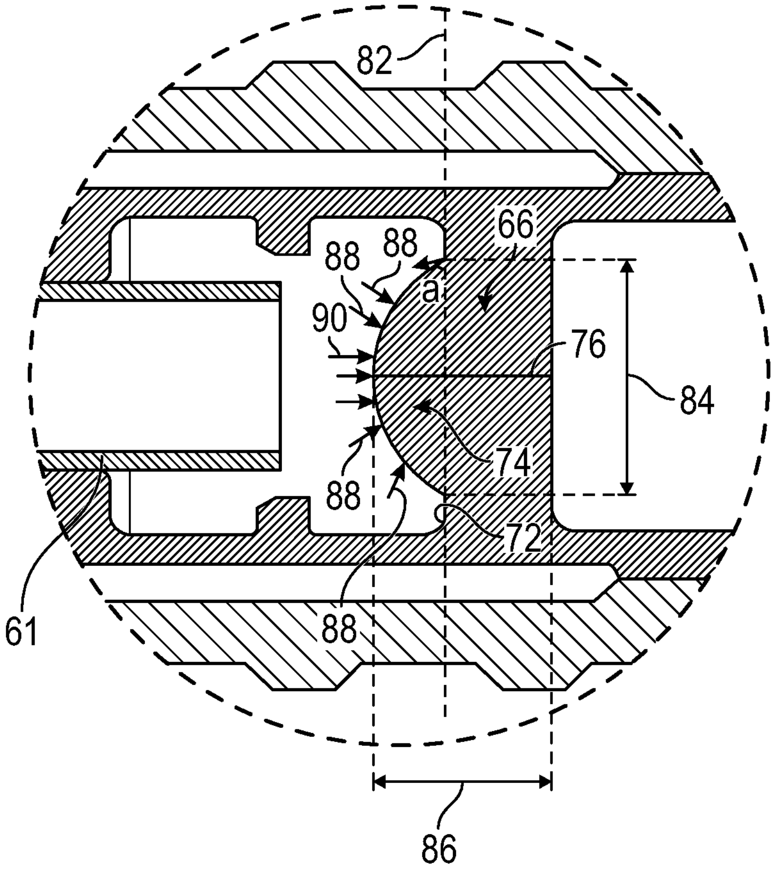
FIG. 2B is an enlarged cross-sectional view of a portion of the catheter assembly of FIG. 2A, according to some embodiments.

Referring now to FIG. 2B, in some embodiments, at least a portion of an outer surface of the protrusion 74 may be disposed at an acute angle a with respect to a transverse axis 82 of the catheter assembly 50. In some embodiments, the transverse axis may be perpendicular to a longitudinal axis of the catheter assembly 50. In some embodiments, the protrusion 74 may include a dome, as illustrated, for example, in FIG. 2B. In some embodiments, a diameter 84 of the dome may be greater than a diameter 86 of the slit 76.

In some embodiments, reflux blood may flow from the vein of the patient through the catheter 59 and into the distal cavity 68. The reflux blood may include a radial component 88 and an axial component 90 which may apply a radial force and an axial force, respectively, on the protrusion 74.

Figure 2C:
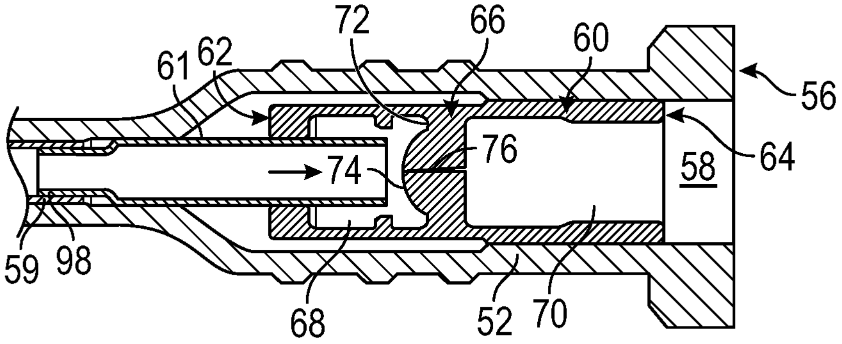
FIG. 2C is a cross-sectional view of the catheter assembly of FIG. 2A, illustrating example opposing slits of the septum pressed against each other more tightly in response to forces from reflux blood flowing proximally through an example septum actuator, according to some embodiments.

Referring now to FIG. 2C, in some embodiments, in response to the reflux blood flowing against the protrusion 74, opposing faces of the slit 76 may press against each other more tightly to seal the slit 76, as illustrated, for example, in FIG. 2C. This may be due to the radial forces of the reflux blood on the protrusion as well as the axial forces of the reflux blood on the protrusion 74. As the axial forces act on a center portion of the protrusion 74, pushing the center portion of the protrusion 74 axially in a proximal direction, the opposing faces of the slit 76, particularly distal ends of the opposing faces, move toward each other in greater interference.

Figure 2D:
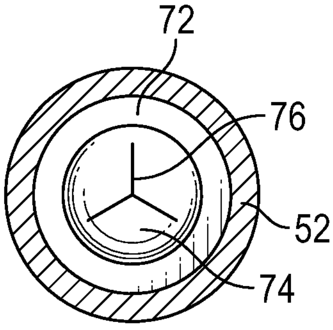
FIG. 2D is a cross-sectional view of the catheter assembly of FIG. 2A along the line 2D-2D, according to some embodiments.

Referring now to FIG. 2D, the slit 76 may include any number of configurations. For example, as illustrated in FIG. 2D, the slit 76 may be Y-shaped. In other embodiments, the slit 76 may be X-shaped. In some embodiments, the slit 76 may be linear.

Figure 2E:
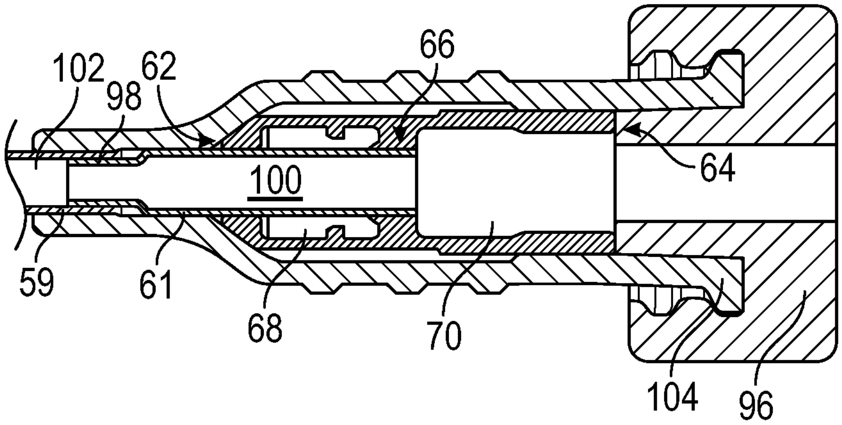
FIG. 2E is a cross-sectional view of the catheter assembly of FIG. 2A, illustrating the septum in a distal position, according to some embodiments.

Referring now to FIG. 2E, in some embodiments, the septum actuator 61 may be fixed within the lumen 58 of the catheter adapter 52. In some embodiments, the septum 60 may be configured to move between a proximal position and a distal position in response to insertion of a separate device into the proximal end 56 of the catheter adapter 52. The separate device may include a luer adapter 96, as illustrated, for example, in FIG. 2E.

In some embodiments, the septum actuator 61 may penetrate the slit 76 when the septum 60 is in the distal position, as illustrated, for example, in FIG. 2E. In some embodiments, the slit 76 may extend through a center of the protrusion 74 such that the septum actuator 61 is disposed within the center of the protrusion 74 when the septum 60 is disposed in the distal position. In some embodiments, the protrusion 74 may be adjacent the septum actuator 61 when the septum 60 is in the proximal position prior to insertion of the separate device, as illustrated, for example, in FIGS. 2A-2C. In some embodiments, the protrusion 74 may contact the septum actuator 61 when the septum 60 is in the proximal position prior to insertion of the separate device.

In some embodiments, the septum actuator 61 may be fixedly positioned within the distal cavity 68 and may include a portion that is positioned adjacent the septum 60 prior to activation of the catheter assembly 50. In some instances, the septum actuator 61 may include a base 98 that is coupled to the catheter adapter 52. For example, as shown, the base 98 can be at least partially inserted into a proximal end of the catheter 59. In some embodiments, the base 98 may act as a wedge forming a press fit between the catheter 59 and the catheter adapter 52 to, at least partially, retain the catheter 59 and the base 98 in place. In some embodiments, the base 98 can be coupled directly to the catheter adapter 52 via a fastener, adhesive, bonding technique, or molding. As shown, the septum actuator 61 may have a tubular configuration with a hollow interior that forms a lumen 100 in fluid communication with a lumen 102 of the catheter 59.

In some embodiments, the proximal end 56 of the catheter adapter 52 includes a flange 104. The flange 104 provides a positive surface which may be configured to enable coupling of intravenous tubing or the luer adapter 96 to the catheter assembly 50. In some embodiments, the flange 104 further includes threading to accept the luer adapter 96 via a threaded connection.

Figure 3:
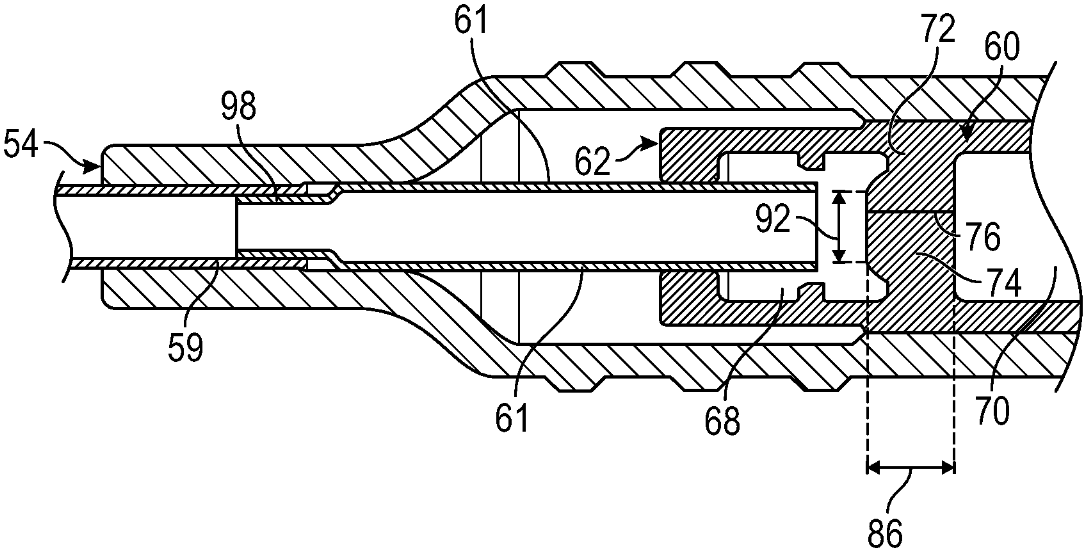
FIG. 3 is a cross-sectional view of the catheter assembly of FIG. 2A, illustrating another example protrusion, according to some embodiments.

Referring now to FIG. 3, in some embodiments, the protrusion 74 may include a truncated dome. In some embodiments, a diameter 92 of a truncated portion of the truncated dome may be greater than the diameter 86 of the slit 76.

Figure 4:
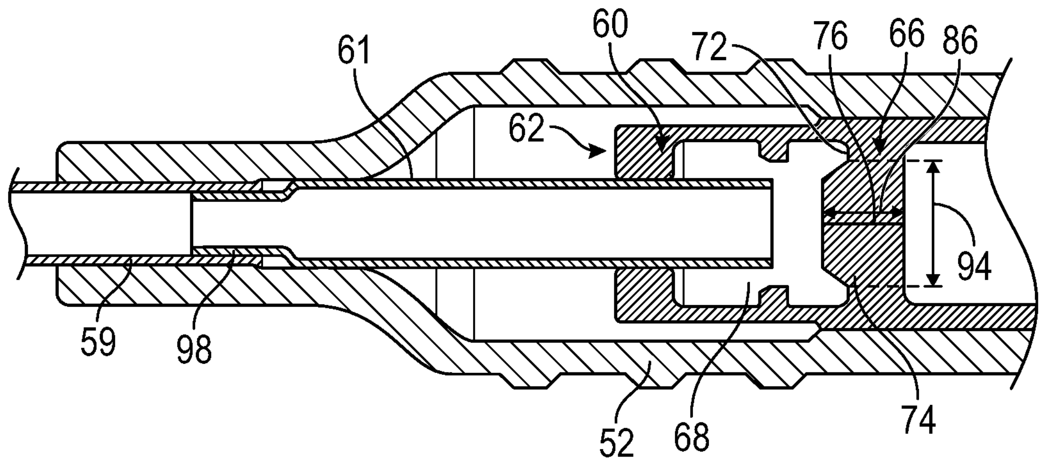
FIG. 4 is a cross-sectional view of the catheter assembly of FIG. 2A, illustrating another example protrusion, according to some embodiments.

Referring now to FIG. 4, in some embodiments, the protrusion 74 may include a truncated cone. In some embodiments, a diameter 94 of a truncated portion of the truncated cone may be greater than the diameter 86 of the slit 76.

Figure 5:
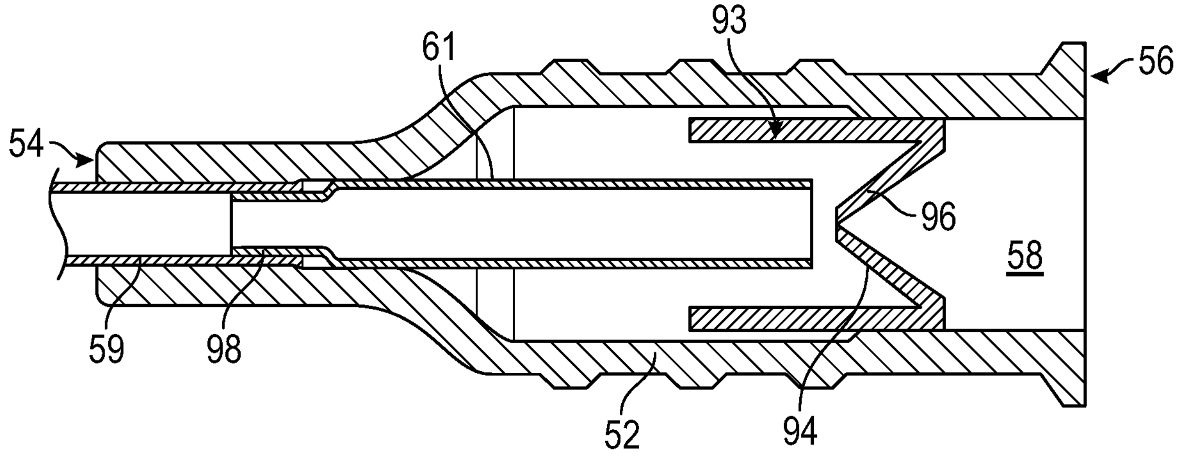
FIG. 5 is a cross-sectional view of the catheter assembly of FIG. 2A, illustrating another septum having a duckbill valve, according to some embodiments.

Referring now to FIG. 5, in some embodiments, another septum 93 that may be used with the catheter assembly 50 may include a duckbill valve 96. A non-limiting example of a duckbill valve is described in U.S. Pat. No. 9,126,012, filed Oct. 3, 2012, entitled "INTRAVENOUS CATHETER WITH DUCKBILL VALVE," which is hereby incorporated by reference in its entirety. In some embodiments, flaps of the duckbill valve 96 may extend inwardly and proximally. In some embodiments, the two inwardly oriented flaps may be pushed apart by the septum actuator 61 to open a gap between the flaps in response to insertion of a luer device, such as, for example, the luer device 96 of FIG. 2E, and movement of the septum 93 to a distal position. In some embodiments, the septum 93 may include or correspond to the septum 60 described with respect to FIGS. 2-5. In further detail, in some embodiments, the septum 93 may include one or more features of the septum 60.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter assembly, comprising:

a catheter adapter comprising a distal end, a proximal end, and a lumen extending therethrough;

a septum actuator positioned within the lumen of the catheter adapter;

a septum slidably disposed within the lumen, the septum comprising a distal end forming a distal cavity into which the septum actuator extends, a proximal end forming a proximal cavity, a barrier disposed between the distal end of the septum and the proximal end of the septum, and a slit disposed within the barrier for selectively opening fluid communication between the distal cavity and the proximal cavity, wherein a distal face of the barrier comprises a protrusion that is contained within the distal cavity and spaced apart from a sidewall that forms the distal cavity, wherein the septum is configured to move between a proximal position and a distal position in response to insertion of a separate device into the proximal end of the catheter adapter, wherein the slit extends through a center of the protrusion such that the septum actuator extends through the center of the protrusion when the septum is disposed in the distal position.

2. The catheter assembly of claim 1, wherein the protrusion contacts the septum actuator when the septum is in the proximal position prior to insertion of the separate device.

3. The catheter assembly of claim 1, wherein the protrusion is adjacent the septum actuator when the septum is in the proximal position prior to insertion of the separate device.

4. The catheter assembly of claim 1, wherein the protrusion comprises a round dome.

5. The catheter assembly of claim 1, wherein the distal end of the septum is secured around the septum actuator.

6. The catheter assembly of claim 1, wherein the protrusion includes a truncated dome.

7. The catheter assembly of claim 6, wherein a diameter of a truncated portion of the truncated dome is greater than a diameter of the slit.

8. The catheter assembly of claim 1, wherein an outer surface of the protrusion is disposed at an acute angle with respect to a transverse axis of the catheter assembly.

9. The catheter assembly of claim 1, further comprising: a catheter that extends distally from the catheter adapter.

10. The catheter assembly of claim 1, wherein a proximal face of the barrier is flat.

11. The catheter assembly of claim 1, wherein the protrusion is symmetric.

12. The catheter assembly of claim 1, wherein in response to reflux blood flowing against the protrusion, opposing faces of the slit press against each other to more tightly to seal the slit.

13. The catheter assembly of claim 1, wherein the slit is Y-shaped.

14. The catheter assembly of claim 1, wherein the slit is X-shaped.

15. The catheter assembly of claim 1, further comprising: an anti-pathogenic material that holds the septum in place within the lumen.

16. The catheter assembly of claim 1, further comprising: a catheter that extends distally from the catheter adapter; wherein a distal end of the septum actuator inserts into a proximal end of the catheter.

17. The catheter assembly of claim 16, wherein the distal end of the septum actuator functions as a wedge for forming a press fit between the catheter and the catheter adapter.

18. The catheter assembly of claim 16, wherein the septum actuator forms a second lumen.

19. The catheter assembly of claim 1, wherein a distal end of the septum actuator is coupled to the catheter adapter.

20. The catheter assembly of claim 1, wherein the septum actuator forms a second lumen that provides the fluid communication between the distal cavity and the proximal cavity.

* * * * *